United States Patent
Abe et al.

[11] Patent Number: 5,209,744
[45] Date of Patent: May 11, 1993

[54] ARTIFICIAL ANUS DEVICE

[76] Inventors: Shosaburo Abe; Yoshikatsu Abe, both of 6-5, Shichirigahama Higashi 3-chome, Kamakura-shi, Kanagawa-ken, Japan

[21] Appl. No.: 712,276

[22] Filed: Jun. 10, 1991

[30] Foreign Application Priority Data

Jun. 13, 1990 [JP] Japan .................................. 2-152650
Sep. 12, 1990 [JP] Japan .................................. 2-240057

[51] Int. Cl.⁵ ............................................... A61F 5/44
[52] U.S. Cl. ..................................... 604/342; 604/338; 604/332
[58] Field of Search .............................. 604/332–345

[56] References Cited

U.S. PATENT DOCUMENTS

| | | | |
|---|---|---|---|
| 2,505,664 | 4/1950 | Edwards | 604/341 |
| 2,549,348 | 4/1951 | Wagner | 604/341 |
| 2,549,649 | 4/1951 | Hove | 604/341 |
| 2,581,319 | 1/1952 | Baxter | 604/341 |
| 2,634,727 | 4/1953 | Nelson | 604/341 |
| 2,684,675 | 7/1954 | Perry | 604/341 |
| 2,784,718 | 3/1957 | Fenton | 604/342 |
| 2,796,063 | 6/1957 | Smelser | 604/342 |
| 2,869,548 | 1/1959 | Mason | 604/342 |
| 2,896,624 | 7/1959 | Candido | 604/342 |
| 2,914,068 | 11/1959 | Schacht | 604/341 |
| 3,439,679 | 4/1969 | Doolittle | 604/344 |
| 4,816,027 | 3/1989 | Gilchrist et al. | 604/342 |

*Primary Examiner*—Randall L. Green
*Assistant Examiner*—R. Clarke
*Attorney, Agent, or Firm*—Armstrong, Westerman, Hattori, McLeland & Naughton

[57] ABSTRACT

An artificial anus device consists of a device body and an excreta receptacle bag, and is fastened to the abdomen of a user with a belt. The device body is provided in its central portion with a through hole into which the excreta receptacle bag and an artificial anus are to be inserted, and on the portion thereof which is around the through hole with an abdomen pressure contacting portion of a predetermined thickness formed integrally therewith. The abdomen pressure contacting portion is provided in the outer circumferential surface of its base part with a recessed locking portion with which the excreta receptacle bag can be detachably engaged. The device body is provided in the portions thereof which are on the left and right sides of and symmetric with respect to the through hole and which are formed integrally with the abdomen pressure contacting portion with locking holes in which both end portions of the belt are locked. The excreta receptacle bag has a cylindrical bag body formed out of flexible rubber or synthetic resin and having at its open end a ring type locking portion to be engaged detachably with the recessed locking portion, and a closed end portion on the opposite side of the open end thereof, the film which constitutes the excreta receptacle bag covering the abdomen pressure contacting portion of and the inner surface of the through hole in the device body, the open end of this bag being engaged detachably with the recessed locking portion.

10 Claims, 9 Drawing Sheets

ARTIFICIAL ANUS DEVICE

BACKGROUND OF THE INVENTION

This invention relates to an artificial anus device used by a person who has had his rectum cut off due to for example rectum cancer, and who has an artificial anus provided with a throwaway excreta receptacle bag, free from the leakage of excreta and a gas while the device is used, and capable of disposing excreta easily.

A conventional commercially available artificial anus device has a mount member formed out of for example a synthetic resin and provided with a pad attached with a double coated adhesive tape to the surface thereof which is on the side of the skin of a user, and an excreta receptacle bag attached with a double coated adhesive tape to the surface thereof which is on the opposite side of the same skin, the device being fixed to the waist of the user with a belt.

The mount member is provided in its central portion with a hole into which an artificial anus is to be inserted, and in the portions thereof which are on the left and right sides of and symmetric with respect to the central hole with locking holes with which both end portions of the belt are to be engaged. The skin-side surface of the mount member is provided with a hollow frustoconical projection extending from the circumferential portion of the central hole. The pad consists of sponge, and is provided in its central portion with a hole into which the artificial anus is to be inserted, and in a hole-surround portion thereof with a plurality of radially extending cuts. The excreta receptacle bag is formed out of vinyl and provided in its side wall with a hole larger than these artificial anus-inserting holes.

However, with the above-described conventional artificial anus device, it is difficult to remove the excreta receptacle bag easily from the mount member with the excreta held in the bag perfectly without causing the excreta to leak to the outside. Moreover, when the user has loose bowels, the excreta receptacle bag has to be replaced frequently, and this very much displeases him who use an artificial anus device out of necessity.

Since the pad which is in contact with the skin of a user in this artificial anus device consists of sponge, a gas leaks therefrom, and the excreta leaks out sometimes to cause the underwear to be soiled or even an offensive odor to be emitted. Since the excreta permeates into the pad, the portion of the skin which is in contact with the pad has often eruption or roughening.

The first named one of the joint inventors of the present invention underwent an operation for rectum cancer about four years ago, and has used a conventional artificial anus device until a recent date but this device has various kinds of problems mentioned above. Under the circumstances, he has taken in his daily life such food that does not cause him to have loose bowels, and restrained himself from going out and making a trip so that the offensive odor emitted from the artificial anus device does not annoy people around him.

SUMMARY OF THE INVENTION

An object of the present invention is to provide an artificial anus device which has an excreta receptacle bag capable of being removed and discarded simply after excreta has gathered therein, without soiling the surroundings, and of being replaced by a new one thereafter, and which is free from the leakage of a gas and excreta and the roughening of the skin of a user.

To achieve this object, the first named inventor of the present invention practically used himself an artificial anus device produced by way of trial, and both of the present inventors have made various improvements to this device repeatedly and made study of the product earnestly and continuously to develop the following means.

The artificial anus device according to the present invention consists of a device body, and an excreta receptacle bag engaged detachably with the device body. The device body is provided with a central through hole, and an abdomen pressure contacting portion and a locking portion which are formed at and in the part of a skin-contacting region of the device body which is around the central through hole. The excreta receptacle bag has a flexible bag body opened at one end thereof and closed at the other.

When the excreta receptacle bag is fastened to a device body, the film constituting the excreta receptacle bag covers the abdomen pressure contacting portion and the inner surface of the central through hole. This excreta receptacle bag is fastened to the device body by detachably engaging the open end portion of the former with the locking portion of the latter. The device body can be provided with a protective projection on the portion of the non-pressure-contacting surface thereof which is around the central through hole. The device body can further be provided with a flexible auxiliary bag detachably so that the auxiliary bag encloses the excreta receptacle bag.

In order to use the artificial anus device of the above-described construction, the excreta receptacle bag is passed through the central through hole in the device body, and the open end portion of the former is fitted in the locking portion provided on the skin-contacting part of the latter. As a result, the abdomen pressure contacting portion and the inner surface of the through hole in this artificial anus device are covered with the film constituting the excreta receptacle bag. The artificial anus device of this structure can be fastened to the body of a user simply by merely inserting the artificial anus into the through hole and fixing the device body to the waist of him with a belt. When excreta has gathered in the excreta receptacle bag, the device body is pulled so as to separate the artificial anus device slightly from the abdomen, and bathroom tissue is rounded and packed in the open end portion of the excreta receptacle bag, which is then removed from the device body and discarded.

DETAILED DESCRIPTION OF THE PREFERRED EMBODIMENTS

First Embodiment

Figure 1:
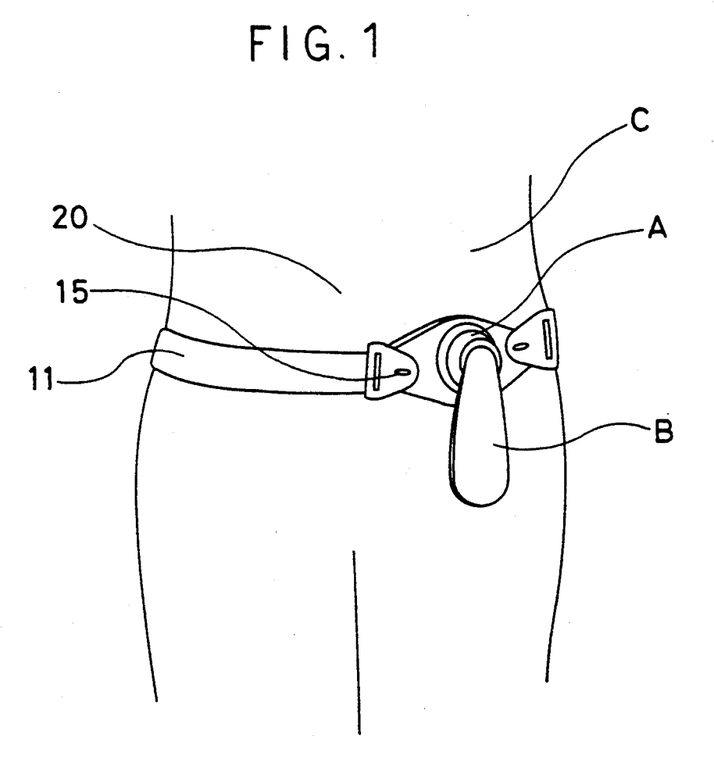
FIG. 1 is a perspective view of an artificial anus device fastened to a human body C.
Figure 2:
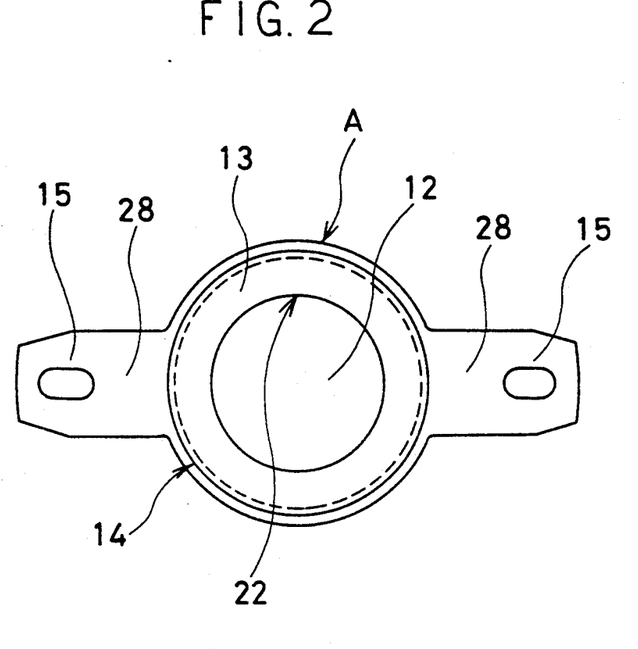
FIG. 2 is a plan view of a device body of a first embodiment of the present invention.
Figure 3:
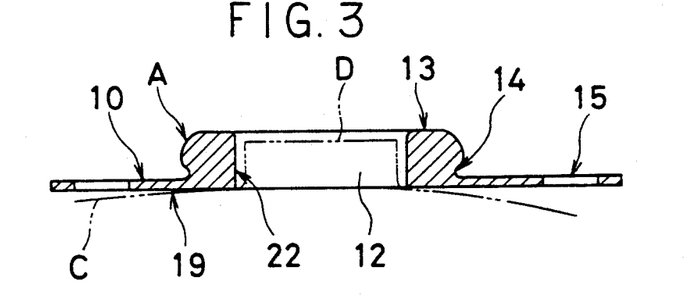
FIG. 3 shows a longitudinal section of the device body of FIG. 2.

FIG. 1 is a perspective view, showing an artificial anus device according to a first embodiment of the present invention fastened to the abdomen 20 of a human body C. This artificial anus device consists of a device body A and an excreta receptacle bag B, and is fastened to the abdomen 20 with a belt 11. As shown in FIGS. 2 and 3, the device body A is provided in its central portion with a through hole 12 into which the excreta receptacle bag B and an artificial anus D are to be inserted, and on the part of the device body A which is around the through hole 12, with an abdomen pressure contacting portion 13 of a predetermined thickness formed integrally therewith.

Figure 4:
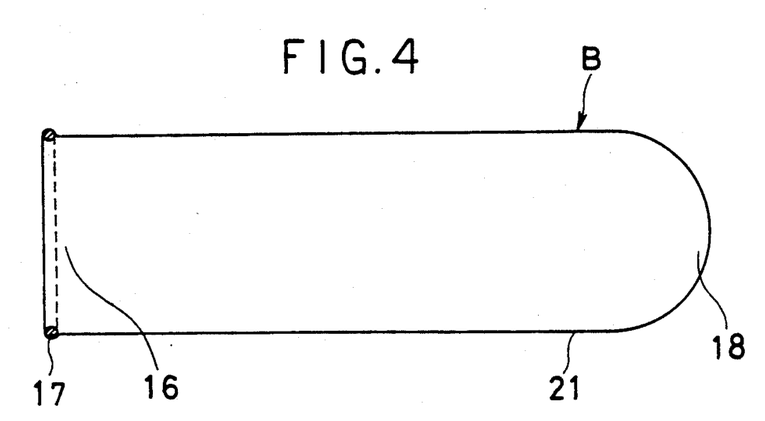
FIG. 4 shows a longitudinal section of an excreta receptacle bag in the first embodiment.

The outer circumferential surface of a base part of the abdomen pressure contacting portion 13 is provided with a recessed locking portion 14 with which the excreta receptacle bag B is to be detachably engaged. The portions of the device body which are integral with the abdomen pressure contacting portion 13 and on the left and right sides of and symmetric with respect to the through hole 12 are provided with locking holes 15 with which both end portions of a belt 11 are to be engaged. As shown in FIG. 4, the excreta receptacle bag B has a cylindrical bag body formed out of flexible rubber or synthetic resin, and is provided at its open end 16 with a ring type locking portion 17 to be detachably engaged with the locking portion 14, the end portion of the bag B which is on the opposite side of the open end 16 forming a closed end portion 18.

Figure 5:
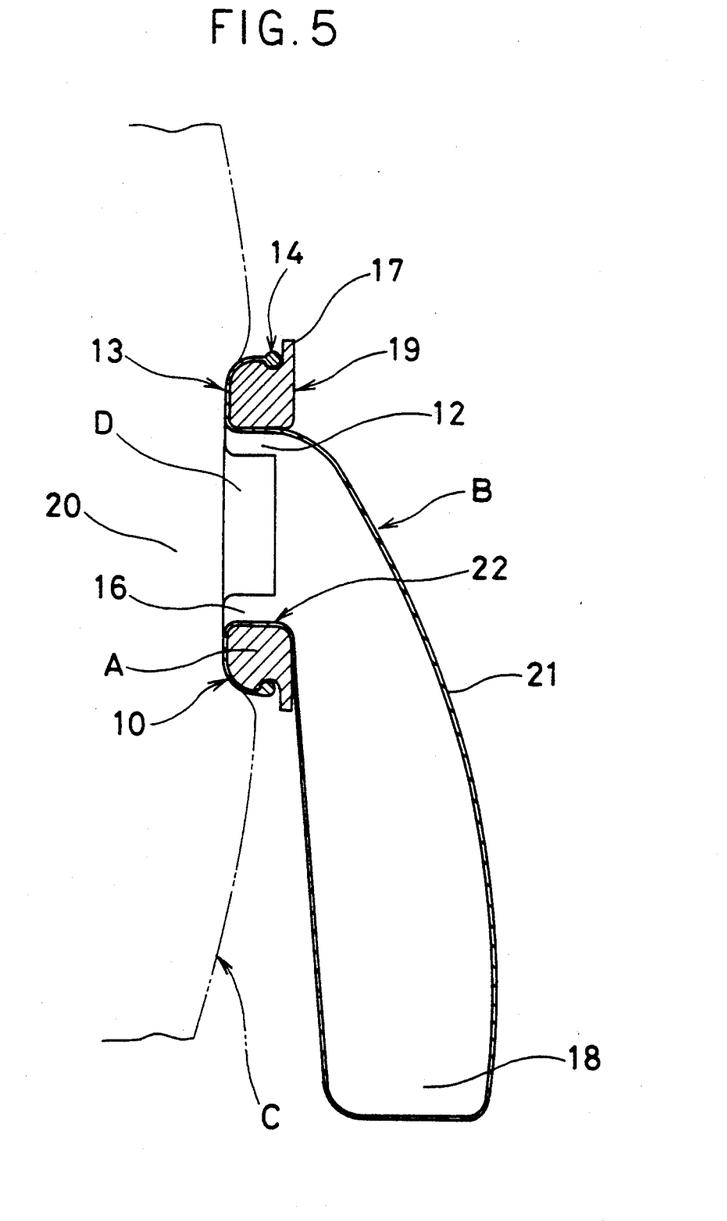
FIG. 5 shows a longitudinal section of the artificial anus device of the first embodiment.

FIG. 5 is a sectional view of the artificial anus device fastened to the abdomen 20 of the human body C. The excreta receptacle bag B is engaged at its flexible locking portion 17 with the locking portion 14 so as to increase the circumferential length of the locking portion 17, and thus fastened to the device body A with the closed end portion 18 passing through the through hole 12 and suspended on a non-pressure-contacting side 19 which is on the opposite side of the abdomen pressure contacting portion 13.

The open end 16 may not be provided in particular with the ring type locking portion 17. It can be engaged with the locking portion 14 by putting the open end 16 over the locking portion 14 and binding the set open end 16 with a rubber band expanded and fitted therearound.

The artificial anus device described above is fastened to the abdomen 20 of the human body C as shown in FIG. 5, by inserting the artificial anus D into the through hole 12, inserting both end portions of the expansible belt 11 into the belt locking holes 15 and tightening the belt 11 so that the device body is pressed moderately against the abdomen 20. Consequently, the whole surface of the comparatively hard abdomen pressure contacting portion 13 is pressed lightly against the soft elastic abdomen 20 via the film 21 of the excreta receptacle bag G to seal the relative portion of the abdomen. Accordingly, the excreta and gas do not leak, and the abdomen 20 has no roughening nor eruption.

Since the film 21 encloses the abdomen pressure contacting portion 13 and the inner surface 22 of the through hole, the device body A is not soiled with the excreta. In order to discard the excreta-containing receptacle bag B, the device body A is held by the hand and separated slightly from the abdomen 20, and bathroom tissue is rounded and packed in the open end 16, the locking portion 17 being then pulled so as to be disengaged from the locking portion 14. The excreta receptacle bag B is then withdrawn through the through hole 12, and discarded. A new excreta receptacle bag B is then fixed to the device body A in the same manner as mentioned above, and the resultant anus device is fastened to the abdomen 20. Since the device body A is not soiled during this time, it need not be washed.

If the belt 11 is tightened a little closely, it may be expansible. Holding down the portions 28 which are between the left and right belt locking holes 15 and locking portion 14 onto adjacent portions of the abdomen 20 with adhesive tapes firmly from the outside so as to reliably maintain the sealed stated between the abdomen 20 and abdomen pressure contacting portion 13 also constitutes a good anus device fastening method.

Figure 6:
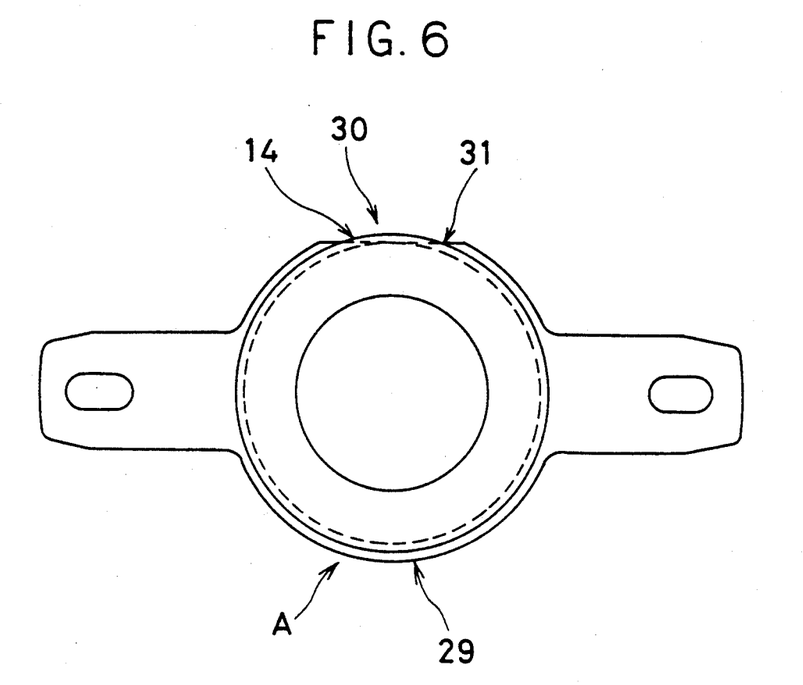
FIG. 6 is a plan view of a modified embodiment of the device body of the first embodiment.
Figure 7:
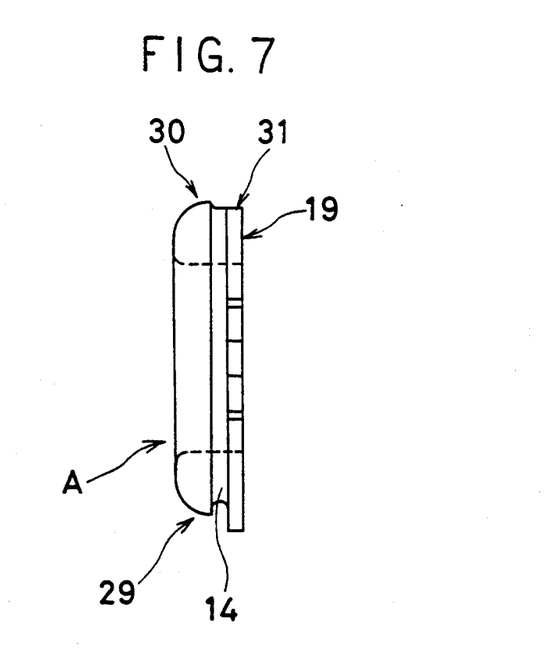
FIG. 7 shows a side elevation of the modified embodiment of FIG. 6.

If the recessed locking portion 14 is formed so that it is deeper at its lower side 29 and shallower at its upper side 30 as shown in FIGS. 6 and 7, and, if the locking portion 17 of the excreta receptacle bag B is fitted in the locking portion 14 first on the lower side 29 thereof, the fastening of the excreta receptacle bag B to the device body A is done more easily.

If the part of the non-pressure-contacting portion 19 which corresponds to the upper side 30 of the locking portion 14 is cut off so that the cut edge is flush with the bottom of the recess in the locking portion 14 to form a cut 31 as shown in FIGS. 6 and 7, the excreta receptacle bag B can be removed from the device body A more simply by disengaging the locking portion 17 of the former first from the cut 31 while pressing the locking portion 17 against the surface of the cut 31.

Second Embodiment

Figure 8:
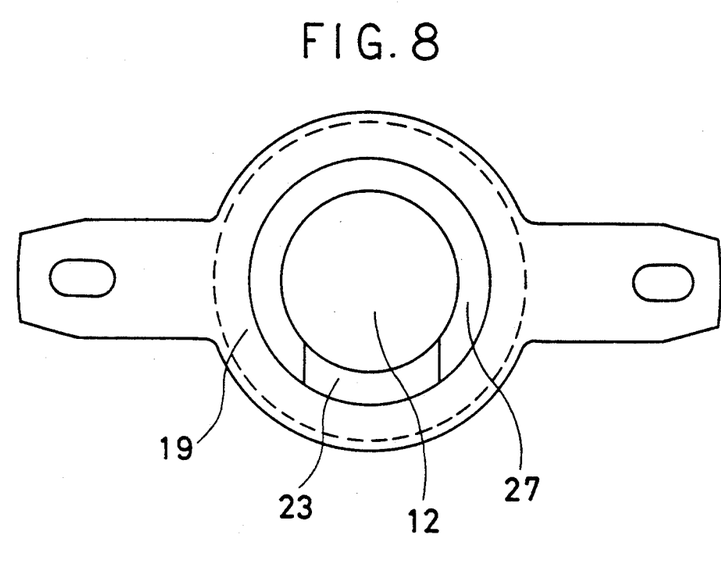
FIG. 8 is a plan view of a device body of a second embodiment of the present invention.
Figure 9:
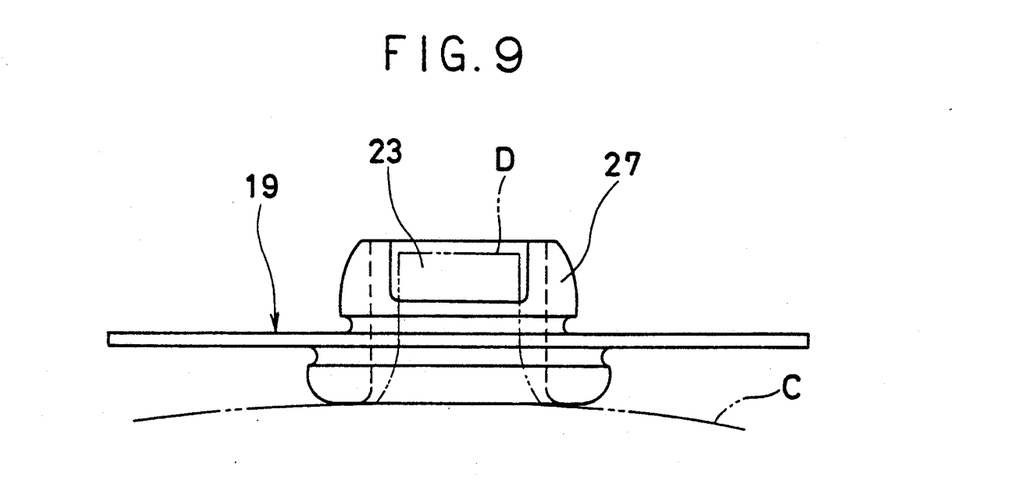
FIG. 9 shows a side elevation of the device body of FIG. 8.

A second embodiment of the present invention will now be described with reference to FIGS. 8 and 9.

The length of a projecting portion, which is beyond the skin of the abdomen 20, of an artificial anus D varies depending upon the results of an operation for rectum cancer, and is generally not more than 5 cm. When the length of a projecting portion is not less than 1 cm, it is desirable that the artificial anus D be protected by providing a protective projection 27 on a non-pressure-contacting portion 19 side. Namely, a tubular protective projection 27 is formed on the part of the non-pressure-contacting portion 19 which is around a through hole 12. A bore 23 is provided in the lower portion of the protective projection 27 so as to guide an excreta receptacle bag B therethrough in the downward direction, whereby the excreta from the artificial anus D is introduced smoothly into the excreta receptacle bag B. When the length of the projecting portion of the protective projection 27 is comparatively small, the cut 23 may not necessarily be provided.

Third Embodiment

Figure 10:
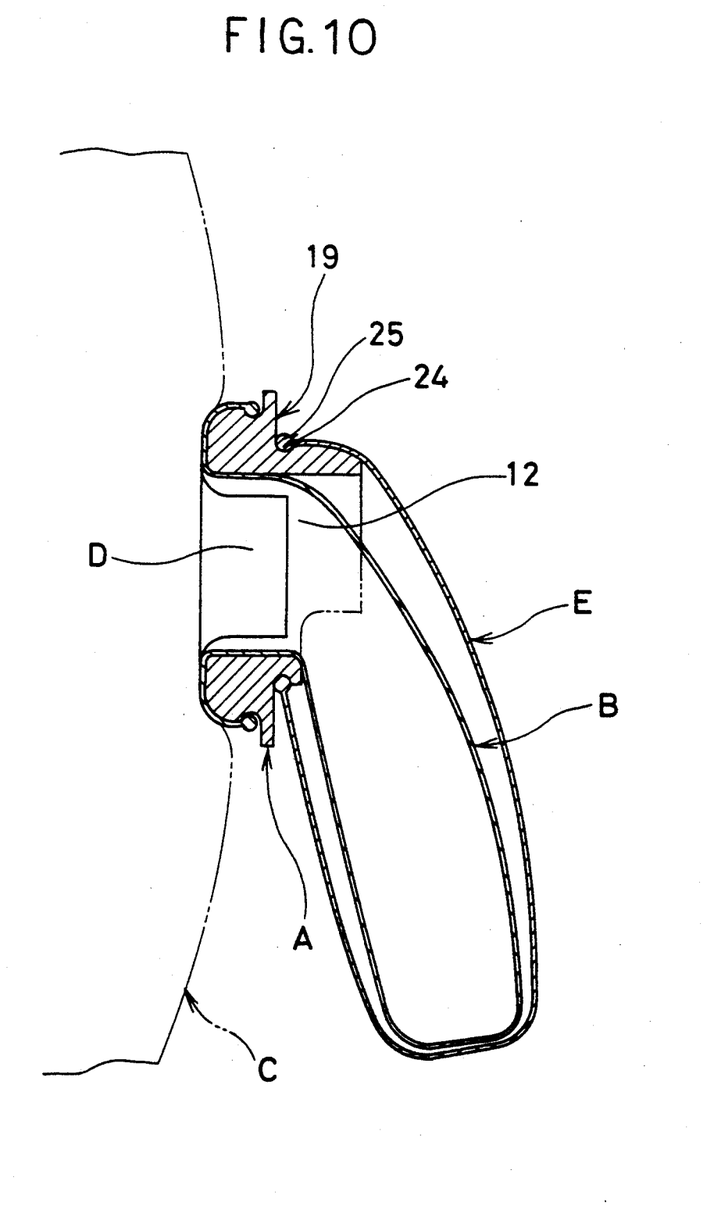
FIG. 10 shows a longitudinal section of an artificial anus device of a third embodiment of the present invention.

A third embodiment of the present invention will now be described with reference to FIG. 10.

An auxiliary bag E is provided over the outer surface of an excreta receptacle bag so as to prevent inconveniences from occurring when the excreta receptacle bag B is broken or holed. Even when the excreta receptacle bag B should be holed or broken, the excreta leakage stops there since the auxiliary bag E is provided over the outer surface thereof. A recessed auxiliary bag locking portion 24 is provided in the part of a device body A which is on a non-pressure-contacting side 19 thereof and around a through hole 12. The auxiliary bag E is then put over the excreta receptacle bag B so as to enclose the same, and a locking portion 25 of the auxiliary bag E is fitted in the locking portion 24, whereby the auxiliary bag E is fastened detachably to the device body A. The auxiliary bag E is formed out of flexible rubber or synthetic resin, and has a one-end-closed bag body, which is provided at its open end with an auxiliary bag locking portion 25.

Figure 11:
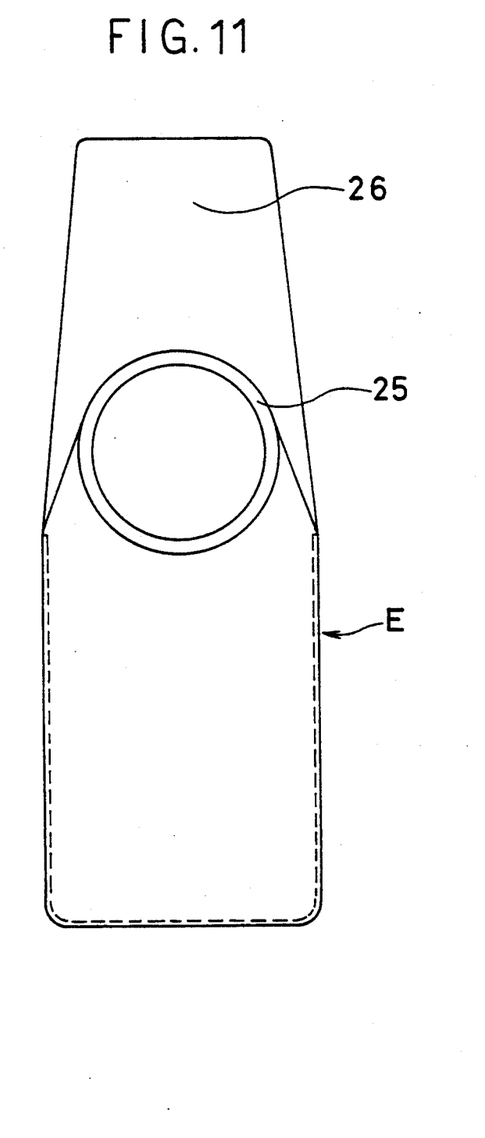
FIG. 11 shows a front elevation of an auxiliary bag in the third embodiment of the invention.
Figure 12:
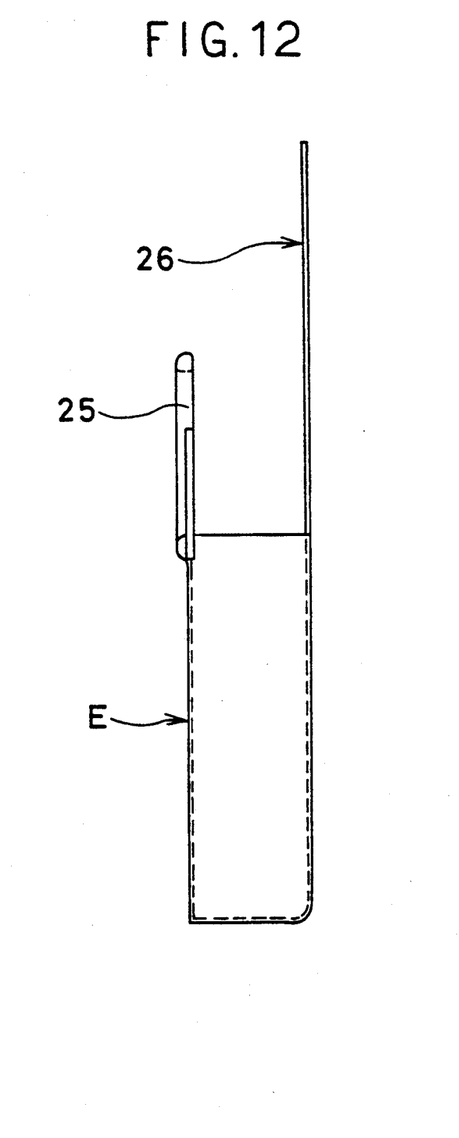
FIG. 12 shows a side elevation of the auxiliary bag of FIG. 11.

FIGS. 11 and 12 show another embodiment of the auxiliary bag E, which is provided with a locking portion 25 at its open end, which is adapted to be engaged with an auxiliary bag locking portion 24, and a flap 26 to be inserted underside of a belt on trousers and fastened thereto.

Fourth Embodiment

A fourth embodiment of the present invention will now be described with reference to FIGS. 13 and 14.

As previously mentioned, the length of a projecting portion beyond the abdomen 20 of an artificial anus D varies depending upon the results of an operation for rectum cancer. This embodiment is adapted to be applied to a person using an artificial anus the projecting portion of which has a comparatively large length.

Figure 13:
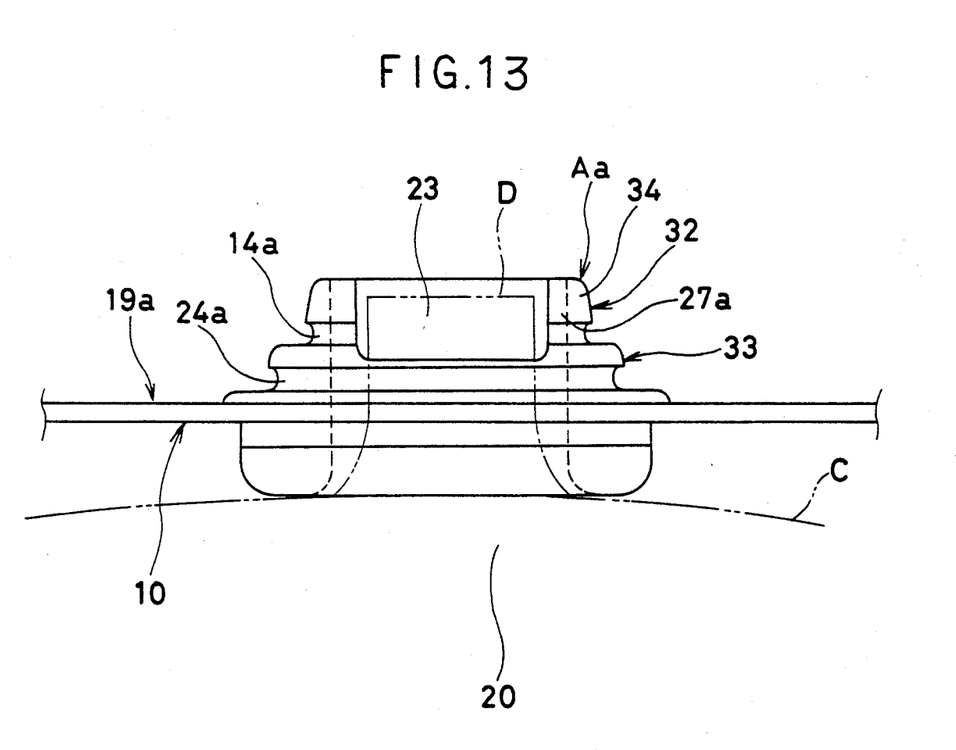
FIG. 13 is a plan view of another embodiment of a protective projection.
Figure 14:
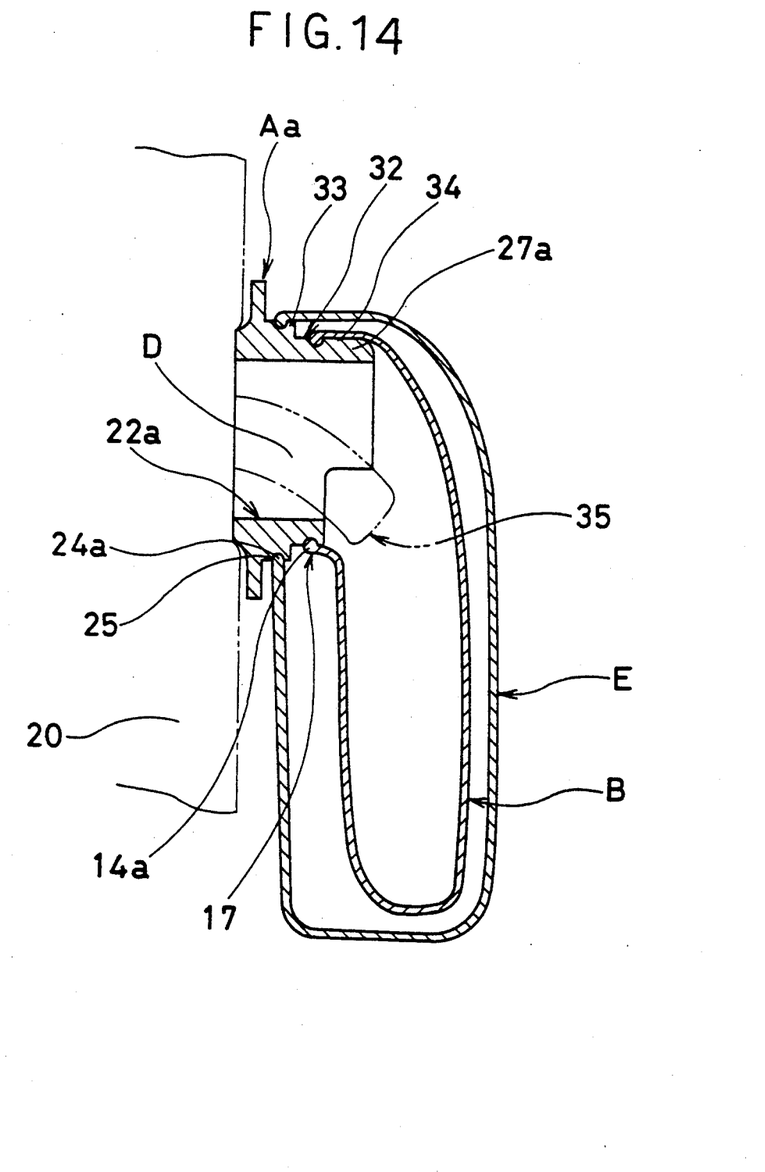
FIG. 14 is a sectional view, showing an excreta receptacle bag and an auxiliary bag which are fastened to a device body.

As shown in FIG. 13, a device body Aa has a protective projection 27a the outer surface 32 of which is formed in a stepped manner. This stepped surface is provided in its larger outer diameter part 33 with a grooved auxiliary bag locking portion 24a, and in its smaller outer diameter part 34 with a locking portion 14a with which an excreta receptacle bag B is engaged. The excreta receptacle bag B and an auxiliary bag E are fastened to the device body Aa by detachably engaging a locking portion 17 with the locking portion 14a, and an auxiliary bag locking portion 25 with the locking portion 24a. When the length of the projecting portion of the artificial anus D is large, the free end 35 thereof extends to the outside of the device body Aa. Therefore, when excreta is discharged from the artificial anus, the device body Aa is not soiled therewith even if the inner surface 22a of a through hole in the device body Aa is not covered with the film 21 of the excreta receptacle bag B. Since the excreta receptacle bag B is engaged with a non-pressure-contacting portion 19a of the device body Aa, the fastening and detaching of the excreta receptacle bag B can be done a little more easily than in the other embodiments in which the excreta receptacle bag B is engaged with the skin side surface 10 of a device body.

As described above, when the artificial anus device according to the present invention is used, the excreta-containing receptacle bag B can be removed simply without soiling the device body A and clothes with the excreta, and replaced with a new one. Moreover, the leakage of a gas and excreta does not occur, nor do the roughening and eruption of the skin of the abdomen 20 occur. When a device body A provided with a protective projection 27 is used, an artificial anus D is not compressed even if the artificial anus D projects far from the surface of the abdomen 20. When a device body provided with an auxiliary bag E is used, the excreta does not leak out even if the excreta receptacle bag B should be holed or broken. Accordingly, this artificial anus device can be used with a sense of relief without worrying about anything.

Since the present invention displays these effects, it is unnecessary for a user to take such food selectively that does not cause him to have loose bowels, and to restrain himself from going out or making a trip so that the offensive odor emitted from the artificial anus device does not annoy others. Therefore, even a person who uses an artificial anus out of necessity can live a daily life in substantially the same manner as an ordinary person.

What is claimed is:

1. An artificial anus device comprising:
   an excreta receptacle bag comprising a flexible bag body made from a thin film and having an opening at one end thereof;
   a device body for securing said receptacle bag to an abdomen, said device body comprising a through hole, one side of said device body comprising an abdomen pressure contacting portion disposed around said through hole and a locking portion comprising an annular recess disposed around an outer circumference of said device body;
   wherein said one side of said receptacle bag is inserted through said through hole and an edge of said opening is detachably engaged in said annular recess such that said thin film covers said abdomen pressure contacting portion and an inner surface of said through hole and said annular recess has a depth deeper on one side of said outer circumference of said device body than on the other side of said outer circumference of said device body.

2. An artificial anus device according to claim 1, wherein a cut edge portion of said device body is provided on another side of said device body opposite said one side and on a non-pressure contacting portion of said device body, wherein the cut edge portion is substantially flush with or slightly higher than a depth of said annular recess.

3. An artificial anus device according to claim 1, further comprising a protective projection formed on an opposite side of said device body around said through hole and projecting in a direction away from said pressure contacting portion.

4. An artificial anus device according to claim 3, further comprising a bore provided in a lower portion of said protective projection.

5. An artificial anus device according to claim 1, further comprising an auxiliary flexible bag fastened detachably to said device body so as to enclose said excreta receptacle bag.

6. An artificial anus device according to claim 1, wherein said excreta receptacle bag comprises a bag body formed from a flexible rubber or synthetic resin and having a locking ring at said open end thereof, wherein said locking ring is securely engageable in said annular recess.

7. An artificial anus device comprising:
an excreta receptacle bag comprising a flexible bag body made from a thin film and having an opening at one end thereof;
a device body for securing said receptacle bag to an abdomen, said device body comprising a through hole, one side of said device body comprising an abdomen pressure contacting portion disposed around said hole, a protective projection formed on an opposite side of said device body around said through hole and projecting in a direction opposite from said pressure contacting portion, and a locking portion comprising an annular recess disposed around an outer circumferential surface of said protective projection;
wherein said one end of said receptacle bag is engaged around said projection and an edge of said opening is detachably engaged in said annular recess and the other circumferential surface of said protective projection comprises a stepped surface, said stepped surface having first and second outer diameter portions, said first outer diameter portion being larger in diameter than said second outer diameter portion, said first outer diameter portion having an auxiliary bag locking portion comprising a first annular recess, and said second outer diameter portion having an excreta bag locking portion comprising a second annular recess.

8. An artificial anus device according to claim 7, further comprising a bore provided in a lower portion of said protective projection.

9. An artificial anus device according to claim 7, further comprising an auxiliary flexible bag fastened detachably to said device body so as to enclose said excreta receptacle bag.

10. An artificial anus device according to claim 7, wherein said excreta receptacle bag comprises a bag body formed from a flexible rubber or synthetic resin and having a locking ring at said open end thereof, wherein said locking ring is securely engageable in said annular recess.

* * * * *